United States Patent
Cerne et al.

(10) Patent No.: US 11,542,078 B2
(45) Date of Patent: Jan. 3, 2023

(54) DEVICE AND METHOD FOR THE PREPARATION AND ORAL ADMINISTRATION OF A LIQUID COMPOSITION

(71) Applicant: DR. SCHAR S.P.A., Postal (IT)

(72) Inventors: Virna Lucia Cerne, Postal (IT); Ombretta Polenghi, Postal (IT); Fabio Barban, Postal (IT)

(73) Assignee: DR. SCHAR S.P.A.

(*) Notice: Subject to any disclaimer, the term of this patent is extended or adjusted under 35 U.S.C. 154(b) by 420 days.

(21) Appl. No.: 16/762,560

(22) PCT Filed: Oct. 30, 2018

(86) PCT No.: PCT/IT2018/050212
§ 371 (c)(1),
(2) Date: May 8, 2020

(87) PCT Pub. No.: WO2019/092765
PCT Pub. Date: May 16, 2019

(65) Prior Publication Data
US 2020/0339325 A1    Oct. 29, 2020

(30) Foreign Application Priority Data
Nov. 9, 2017   (IT) .................. 102017000128170

(51) Int. Cl.
*B65D 51/28*      (2006.01)
*A61K 31/198*     (2006.01)
*A61J 1/20*       (2006.01)

(52) U.S. Cl.
CPC ........ *B65D 51/2821* (2013.01); *A61J 1/2048* (2015.05); *A61J 1/2089* (2013.01); *A61K 31/198* (2013.01); *B65D 51/2828* (2013.01)

(58) Field of Classification Search
CPC ............ B65D 51/2821; B65D 51/2828; A61J 1/2048; A61J 1/2089; A61K 31/198
See application file for complete search history.

(56) References Cited

U.S. PATENT DOCUMENTS

| | | | |
|---|---|---|---|
| 5,587,399 A * | 12/1996 | Acosta | A23L 33/16 514/474 |
| 6,098,795 A * | 8/2000 | Mollstam | B65D 5/748 206/219 |
| 2010/0237075 A1* | 9/2010 | Wilhelm | B65D 47/243 220/284 |
| 2016/0317388 A1* | 11/2016 | Bhargava | A61K 9/10 |

* cited by examiner

Primary Examiner — Timothy P. Kelly
(74) Attorney, Agent, or Firm — Maine Cernota & Rardin

(57) ABSTRACT

The invention concerns a device and a method for the preparation of a liquid composition for oral administration of a liquid composition formed by a liquid component and a component in powder form, for the treatment of persons affected by metabolic disorders, in particular appropriately selecting the compounds to be added to the drink according to the specific metabolic disorder.

16 Claims, 3 Drawing Sheets

DEVICE AND METHOD FOR THE PREPARATION AND ORAL ADMINISTRATION OF A LIQUID COMPOSITION

RELATED APPLICATIONS

This application is a national phase application filed under 35 USC § 371 of PCT Application No. PCT/IT2018/050212 with an International filing date of Oct. 30, 2018, which claims priority of IT Patent Application 102017000128170 filed Nov. 9, 2017. Each of these applications is herein incorporated by reference in its entirety for all purposes.

FIELD OF THE INVENTION

Embodiments described here concern a device and method for the preparation and administration of a liquid composition, in particular for the treatment of persons or individuals affected by rare metabolic or non-metabolic disorders.

In particular, embodiments described here concern a device and a method that allow to prepare quickly and simply a liquid composition, or drink, suitable for those affected by a rare metabolic or non-metabolic disorder, and to select in an appropriate manner the compounds to be added to a liquid composition, or drink, to be taken depending on the specific disorder to be treated.

BACKGROUND OF THE INVENTION

The existence of rare metabolic disorders that entail an abnormal metabolic behavior with regard to some substances to be metabolized, such as amino acids, fats or carbohydrates, is known.

This metabolic alteration causes an accumulation of the substance to be metabolized or its by-products, and this can cause toxic action in different parts of the body. The organs most affected by these rare metabolic disorders are the central and peripheral nervous system, the liver and the kidneys.

In many countries, newborns are subjected to screening in the first days after birth in order to identify the presence of a possible metabolic disorder and, if necessary, to start pharmacological treatment and a controlled diet as soon as possible.

The main treatment in almost all rare metabolic disorders is the elimination or significant reduction in the diet of the specific substance, such as an amino acid, a sugar or a type of fat, which the patient is not able to metabolize. In the case, for example, of metabolic disorders affecting the amino acids, the diet of the patients provides to eliminate foods that are naturally rich in proteins (meat, fish, milk, eggs, etc.), as well as to consume foods with very low quantities of proteins. Moreover, the integration of daily protein requirements occurs through the administration of food for special medical purposes containing nutritional substances, with the exclusion of the substance that is toxic for the organism of the person affected by a metabolic disorder.

These foods are also enriched with macro- and micro-nutrients, which can vary depending on the age of the patient: for example, a product intended for unweaned infants generally has a high quantity of fats and carbohydrates (especially lactose) and a limited quantity of proteins to mimic the composition of breast milk. A product intended for children and adults has fewer fats and a greater quantity of amino acids.

Similarly the profile of minerals, trace elements and vitamins varies in the different product ranges to meet the nutritional needs of patients from birth until adulthood.

The dietician must calculate for each patient the daily protein requirements necessary for growth and the normal turn-over of the proteins of the organism, based on the age, weight, and sex of the patient.

The most widespread rare metabolic disorders are those affecting the amino acids, therefore they imply a difficulty on the part of the human organism in metabolizing one or more amino acids. Among them we can mention phenylketonuria (PKU), tyrosinemia (TYR), homocystinuria (HCys) and organic acidemias: these can occur as maple syrup urine disease (MSUD), methylmalonic and propionic acidemia (OAc), isovaleric acidemia (LEU).

Other rare metabolic disorders can concern an altered carbohydrate metabolism, such as glucose and galactose intolerance, or an altered metabolism of certain lipids, such as for example oxidation disorders of the fatty acids.

We will now give a brief description of the rare metabolic disorders affecting amino acids listed above, and their effects on the human body.

Phenylketonuria (PKU) is a rare metabolic disorder caused by a deficiency in the metabolism of phenylalanine. A deficit in the enzyme phenylalanine hydroxylase or in its cofactor tetrahydrobiopterin causes an anomalous accumulation of phenylalanine in body fluids and in the central nervous system, which is the zone most affected by this pathology. Depending on the residual capacity to metabolize phenylalanine and therefore on the blood concentration of this amino acid, the disorder is classified as severe, moderate or mild. If the blood concentration of phenylalanine is not controlled, patients are subject to cognitive impairment and irreversible mental retardation (Williams, Mamotte, & Burnett, 2008).

Following the diagnosis of the disorder, a more or less restrictive aprotein diet must be initiated depending on the patient's residual enzymatic activity and the protein intake must be supplemented with special medical foods without phenylalanine.

Tyrosinemia (TYR), a metabolic disorder affecting tyrosine metabolism, exists in three variants: type I, type II and type III characterized respectively by a defect in the enzyme fumarilacetoacetate hydrolase (FAH), tyrosine aminotransferase and p-hydroxyphenylpyruvic dioxygenase acid. Some toxic tyrosine metabolites interfere with normal metabolic processes in different body zones. If the disorder is not treated, the patient will experience progressive liver damage, kidney damage, peripheral seizures, hepatocellular carcinoma and the formation of crystals in the cornea. Life expectancy in the absence of pharmacological or dietetic treatment or liver transplantation is less than ten years. The treatment involves the drug therapy with Nitisinone associated with the restriction of proteins in the diet, which are replaced by food for special medical purposes without tyrosine and phenylalanine, which is a precursor of tyrosine itself (Alobaidy, 2017).

Homocystinuria is a disorder caused by the defect of the enzyme cystathionine betasyntaxis that metabolizes methionine. There are two forms of the pathology: a milder form in which the patient responds to therapy with vitamin B6, and a more severe form that is insensitive to this treatment. The pathology leads to delayed development, intellectual disability, ectopia lentis, severe myopia, skeletal anomalies and a high risk of thromboembolism. The treatment provides to administer vitamin B6 in B6-responsive patients and to restrict natural proteins in the diet substituted by food without methionine (Ladys & Street, 2005).

Maple syrup urine disease (MSUD) is a metabolic disorder that is part of organic acidemias. In this pathology, the patient has a genetic defect that affects the branched chain alpha-ketoacid dehydrogenase complex. This protein complex is necessary for the proper metabolism of leucine, isoleucine and valine (branched chain amino acids).

The pathology is divided into classic, intermediate, intermittent and thiamine-responsive MSUD. Classic MSUD occurs in the first days of life with encephalopathy, coma and respiratory arrest. Patients can suffer from intoxications and metabolic crises consequent to an increase in protein degradation (infection, surgery, wounds, psychological stress). MSUD therapy provides to administer thiamine if the patient responds to this treatment, or to restrict the diet and use foods without the branched chain amino acids leucine, isoleucine and valine (Chuang, Chuang, & Wynn, 2006).

Methylmalonic acidemia and propionic acidemia (OA) have in common that it is impossible to correctly metabolize the following amino acids: isoleucine, valine, methionine and threonine.

Methylmalonic acidemia is caused by a defect in the methylmalonyl coenzyme A mutase or in the transport/synthesis of its adenosyl cobalamin cofactor or by a defect in the methylmalonyl coenzyme A epimerase. This pathology can manifest in three forms: the non-B12-responsive infantile form, in which the symptoms appear at birth, the intermediate B12-responsive form, in which the symptoms appear after a few weeks or months of life, and the mild form due to a deficiency of methylmalonyl coenzyme A epimerase.

The disorder manifests with episodes of metabolic decompensation in apparently healthy patients. Among the secondary complications are intellectual disabilities, renal dysfunction, neurological problems, optic nerve atrophy and others. Treatment provides to administer vitamin B12 in patients who respond to this therapy, and in all cases to restrict the diet with administration of foods without isoleucine, valine, methionine and threonine (Baumgartner et al., 2014).

Propionic acidemia is caused by a defect in the propionyl coenzyme A carboxylase. The disorder can occur in neonatal age or later depending on different factors (residual enzymatic activity, intake of propiogenic precursors, catabolic stress factors). In the neonatal form, the patient has symptoms of lethargy, poor appetite, vomiting, hypotonia and may have encephalopathy and cardiorespiratory arrest if not treated. When the disorder occurs later, there may be delayed development, intellectual disability, poor growth, gastrointestinal problems, protein intolerance, acute psychosis, hypotonia, and movement disorders. Treatment of the pathology provides a low protein diet and the use of foods rich in amino acids except isoleucine, valine, methionine and threonine (Baumgartner et al., 2014).

Finally, isovaleric acidemia (LEU) is due to a malfunction of the enzyme isovaleryl coenzyme A dehydrogenase, involved in leucine metabolism. There are three forms of the disorder: the acute neonatal form, the intermittent chronic form and the mild asymptomatic form. In the most severe forms, the pathology manifests with vomiting and lethargy which can degenerate into a coma and death of the newborn. The chronic form is associated with retarded development. Both forms have acute episodes of decompensation during metabolic crises (Vockley, Jerry, Ensenauer, 2009). The therapy provides to restrict the diet with carnitine supplementation, glycine and a mixture of leucine-free amino acids.

As seen, in all metabolic disorders affecting the amino acids described above the remedy is based on the patient's intake of specific foods rich in amino acids, with the exclusion of the amino acids that cause the pathology. Foods for the treatment of the most frequent metabolic disorders are mostly in the form of powder to be reconstituted with water, but also ready-to-use liquid or semi-liquid products are marketed. The latter contain a certain quantity of carbohydrates, are enriched in mineral salts, trace elements and vitamins and are often a source of omega 3 and/or omega 6 fats.

While for phenylketonuria, which is the most frequent rare metabolic disorder among those mentioned, there is an ample supply of liquid products on the market both as regards the brands available and as regards the aromatizations; for other rare disorders, patients' choice is often limited to a few powdered products, one or two flavors at most, considering that the products are unlikely to be liquid. This is due to the fact that the incidence in the population of these pathologies is so rare that it is not viable for a food company to produce these products, especially in liquid form.

Another problem that limits the production of these liquid formulations concerns the fast degradation of some nutrients in these products in liquid form.

The above disadvantages generally apply also to formulations and production processes of the formulations for the treatment of non-metabolic disorders. In particular, it is known that there are disorders other than rare metabolic disorders in which an adaptation of the diet can help improve the patient's clinical picture. This is the case, for example, of kidney pathologies, in which a reduction of protein intake by means of a hypoproteic diet can avoid overloading kidneys that are already compromised by a limited filtration capacity. In another example, the treatment of pathologies such as drug-resistant epilepsy is assisted by the total or partial elimination of carbohydrates from the diet and an increase in the intake of fats, in order to promote ketogenesis and obtain energy from lipids, to the detriment of sugar metabolism. The possibility of using this type of diet, defined in specific cases as ketogenic diet, is also under study in the therapeutic support for pathologies such as some gastrointestinal disorders, some types of cancer and Alzheimer's disease.

Document U.S. Pat. No. 6,098,795 describes a device for adding a first component to a second component present in a main package. This known device keeps the first component separated from the second component until the moment of use. Document EP-A-2.160.338 describes a closing stopper with a sealed release chamber for an additive for a drink. Document US-A-2010/237075 describes a perforator for a sheet material for a stopper of a push-pull type container. However, none of these known documents describes the preparation and oral administration of liquid compositions with a precise nutritional profile, intended for the treatment of people affected by metabolic or non-metabolic disorders.

In light of the shortcomings highlighted, the need is felt to make available for people affected by metabolic and also non-metabolic disorders like those described above for example, a device and a method that are simple and effective for the preparation and oral administration of liquid compositions with a precise nutritional profile, intended for the treatment of people affected by metabolic or non-metabolic disorders.

In particular, one purpose of the present invention is to make available a simple and effective device and method for the preparation and oral administration of liquid compositions suitable for those affected by these pathologies, a device and method which are able to diversify liquid compositions or drinks depending on the metabolic or non-metabolic pathology to be treated.

Another purpose of the invention is to make available a device and a method that are advantageous and effective for diversifying the liquid compositions or drinks suitable for a specific metabolic or non-metabolic disorder, according to the aromatic substances added.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, embodiments described here concern a device for the preparation and oral administration of a liquid composition formed by a liquid component and a component in powder form, for the treatment of persons affected by metabolic disorders.

According to one embodiment, the device can be provided for the preparation and oral administration of a liquid composition formed by a liquid component and a component in powder form, for the treatment of persons affected by metabolic disorders comprised in a group consisting of: phenylketonuria, tyrosinemia, homocystinuria, maple syrup urine disease, methylmalonic acidemia, propionic acidemia and isovaleric acidemia.

In some embodiments, the device described here comprises:
a) a bottle inside which there is a liquid component with a pre-established and non-variable composition, irrespective of the type of metabolic disorder to be treated;
b) a closing device configured to close the bottle and inside which there is a component in powder form with a variable composition according to the disorder and functional for the treatment of the specific disorder selected on each occasion;
c) transfer means associated with the closing device and configured to selectively transfer the component in powder form from the closing device to the bottle so as to mix or disperse the liquid component with the component in powder form inside the bottle in order to obtain the liquid composition.

Other embodiments also concern a method for the preparation of a liquid composition formed by a liquid component and a component in powder form, for oral administration for the treatment of persons affected by metabolic or non-metabolic disorders.

According to one embodiment, the method can be provided for the preparation and oral administration of a liquid composition formed by a liquid component and a component in powder form, for the treatment of persons affected by metabolic disorders comprised in a group consisting of: phenylketonuria, tyrosinemia, homocystinuria, maple syrup urine disease, methylmalonic acidemia, propionic acidemia and isovaleric acidemia.

In some embodiments, the method described here comprises the following steps:

a) filling a bottle with a liquid component with a pre-established and non-variable composition irrespective of the type of disorder to be treated;
b) making available a closing device of the bottle, there being present inside the closing device a component in powder form with a variable composition according to the metabolic disorder to be treated and functional for the treatment of the specific disorder selected on each occasion, wherein the bottle and the closing device are coupled to close the bottle;
c) selectively transferring the component in powder form from the closing device to the bottle;
d) mixing or dispersing the liquid component with the component in powder form inside the bottle, advantageously, even if not exclusively, at the moment of consumption.

The method according to the embodiments described here can be used to prepare specific liquid compositions suitable for the treatment of persons affected by metabolic disorders or even non-metabolic disorders, which cause an abnormal metabolic behavior toward some substances, which can be amino acids, fats or carbohydrates.

Therefore, the method according to embodiments described here can be applied to rare metabolic disorders or to non-metabolic disorders, described above in relation to the state of the art. As will be described in detail below, the device and the method according to embodiments described here allow to prepare liquid compositions, or drinks, diversified and specific for persons affected by, for example, one of the following metabolic disorders: phenylketonuria, tyrosinemia, homocystinuria, maple syrup urine disease, methylmalonic acidemia, propionic acidemia and isovaleric acidemia. Or, the following non-metabolic disorders can be treated by the device and the method according to embodiments described here: renal pathologies, pathologies such as drug-resistant epilepsy. The Applicant is also studying the possibility of using the device and method described in other pathologies, such as gastrointestinal disorders, some types of cancer as well as Alzheimer's disease.

In order to carry out the method according to the invention, the device according to the present description is conveniently used, which provides the bottle or vial provided with the closing device, such as a cap or a lid: a suitable amount of the component in powder form is disposed inside. Preferably, the component in powder form is sealed hermetically in a suitable tank or containing capsule disposed inside the closing device. The tank is configured to open selectively, or is frangible, to allow the component in powder form to be transferred from the closing device into the bottle, where it is mixed or dispersed in the liquid component present therein.

As far as the liquid component is concerned, as already said it is present, for example it is fed or generically introduced into the bottle or vial.

The closing device comprises in particular transfer means having the function of transferring, for example, but not restrictively, at the time of consumption of the liquid composition, the component in powder form from the closing device to the bottle below, containing the liquid component, as described above.

The liquid component introduced or present in the bottle can be, in some embodiments, substantially an aqueous solution comprising mineral salts, carbohydrates and universally metabolizable amino acids: the nutrients present in the aqueous solution are stable substances during their shelf life and suitable for different metabolic disorders.

By "universally metabolizable amino acids" in the present description we mean amino acids that are not responsible for the occurrence of the rare metabolic disorders listed above. Therefore, these amino acids can be metabolized without problems by any patient affected by the pathologies indicated.

As explained in relation to the state of the art, the rare metabolic disorders are caused by an alteration of the regular metabolism of one or more amino acids. The amino acids that can be subject to this alteration and therefore cause the above metabolic disorders are the following: phenylalanine, isoleucine, leucine, methionine, threonine, tyrosine and valine.

Advantageously, in the case of disorders affecting the amino acids, the method and device of the present invention provide to dispose a component in powder form comprising a specific mixture of amino acids, chosen according to the specific metabolic disorder, inside the closing device of a bottle. Therefore, this mixture of amino acids will be totally free of the specific amino acid responsible for the specific metabolic disorder. Furthermore, the ingredients inserted in the component in powder form are also the most sensitive during their shelf life. By keeping these ingredients separate from the liquid formulation, it ensures greater stability over time.

Consequently, the method for preparing a drink according to the invention allows to easily and effectively modulate the composition of the component in powder form present in the closing device, suitably adapting it to the specific metabolic or non-metabolic disorder, according to the case, while the composition of the liquid present in the vial remains substantially unchanged for all disorders.

This represents an advantage in terms of productivity from the industrial point of view, since for the passage, for example, from the production of a drink suitable for tyrosinemia to a liquid composition or drink suitable for isovaleric acidemia, step a) of filling the bottle with the liquid component remains unaltered, while only the composition of the component in powder form introduced into the closing device (step b) is changed.

In accordance with other embodiments, the preparation method can be used to make a sequence of liquid compositions, or drinks, suitable to be taken by a person affected by a specific disorder, but diversified with respect to each other as regards the flavor or taste, therefore having differentiated aromas. This can be achieved in step b) by feeding a component in powder form containing specific flavoring substances, while the other components, for example including the amino acids, remain unaltered.

It is clear that what has been described above and the connected advantages, is also applied in the case where the device and the method according to embodiments described here are used, appropriately selecting the component in powder form present in the closing device and the liquid component present in the bottle, also for the preparation and oral administration of liquid compositions suitable for the treatment of persons or individuals affected by non-metabolic disorders, in particular: kidney diseases, pathologies such as drug-resistant epilepsy, pathologies such as some gastrointestinal disorders, or some types of cancer as well as Alzheimer's disease.

Another aspect concerns a kit of containing devices for the preparation of a series of liquid compositions formed by a liquid component and a component in powder form, for the treatment of people affected by metabolic or non-metabolic disorders.

According to some embodiments, a kit of containing devices can be provided for the preparation of a series of liquid compositions formed by a liquid component and a component in powder form, for the treatment of persons affected by metabolic disorders comprised in a group consisting of: phenylketonuria, tyrosinemia, homocystinuria, maple syrup urine disease, methylmalonic acidemia, propionic acidemia and isovaleric acidemia.

In embodiments of the kit described here, each containing device comprises:
- a bottle inside which there is a liquid component with a pre-established and non-variable composition, irrespective of the type of disorder;
- a closing device configured to close the bottle and inside which there is a component in powder form with a variable composition according to the disorder and functional for the treatment of the specific metabolic disorder selected on each occasion and also comprising one or more aromatizing substances;
- transfer means associated with the closing device and configured to transfer the component in powder form in from the closing device to the bottle so as to mix or disperse the liquid component with the component in powder form inside the bottle in order to obtain the liquid composition;

wherein the component in powder form differs, between the closing devices, only in at least one aromatizing substance, the other ingredients of its composition remaining unaltered.

According to some embodiments, relating both to the device, the method and also to the kit, according to the present description, the liquid component is an aqueous solution comprising mineral salts, carbohydrates, aromas and universally metabolizable amino acids.

According to other embodiments, relating both to the device, the method and also to the kit, in accordance with the present description, the component in powder form comprises vitamins and a mixture of amino acids without the specific amino acid responsible for the specific metabolic disorder to be treated comprised in the metabolic disorders. Moreover, according to some embodiments, relating both to the device, the method and also to the kit, in accordance with the present description, the component in powder form is hermetically sealed in a tank or cylindrical chamber inside the closing device.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some embodiments, given as a non-restrictive example with reference to the attached drawings wherein.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Figure 1:
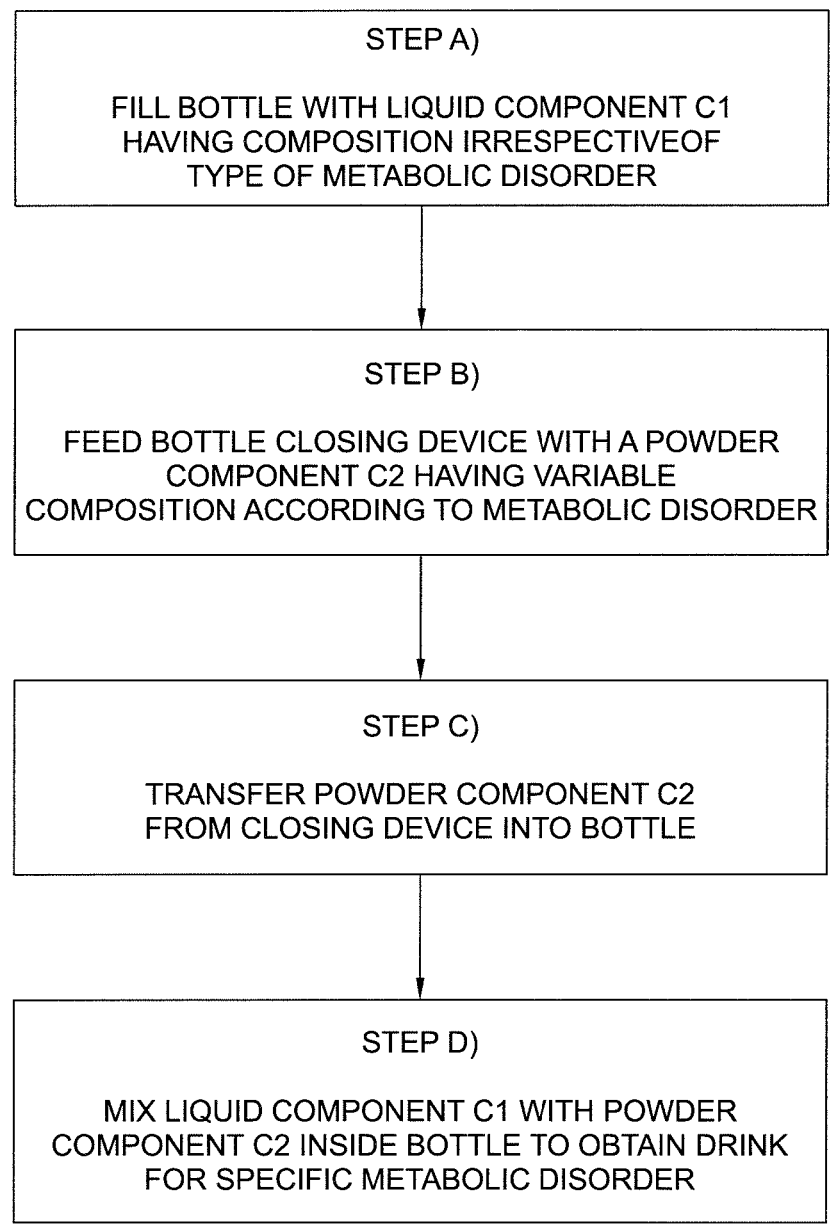
FIG. 1 is a block diagram of the sequence of operating steps needed to implement embodiments of the method according to the present description.

We will now refer in detail to the various embodiments of the present invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall include all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Embodiments described here concern a device 10 for the preparation and oral administration of a liquid composition formed by a liquid component C1 and a powder component C2, for the treatment of persons affected by metabolic or non-metabolic disorders. According to one embodiment, the device 10 comprises:

a) a bottle 11, 31 inside which there is a liquid component C1 having a pre-determined and non-variable composition, irrespective of the type of disorder;

b) a closing device 12, 32 configured to close the bottle 11, 31 and inside which there is a powder component C2 having a variable composition according to the disorder and functional for the treatment of the specific disorder selected on each occasion;

c) transfer means associated with the closing device 12, 32 and configured to selectively transfer the powder component C2 from the closing device 12, 32 to the bottle 11, 31 for the purpose of mixing or dispersing the liquid component C1 with the powder component C2 inside the bottle 11, 31 to obtain the liquid component C1.

According to other embodiments, a method is provided for the preparation of a liquid composition formed by a liquid component C1 and a powder component C2, for the purposes of oral administration for the treatment of persons affected by metabolic or non-metabolic disorders. According to one embodiment, the method comprises the following steps:

a) filling a bottle 11, 31 with a liquid component C1 having a pre-determined and non-variable composition, irrespective of the type of disorder;

b) providing a closing device 12, 32 to close the bottle 11, 31; inside the closing device 12, 32 there is a powder component C2 having a variable composition according to the disorder and functional for the treatment of the specific disorder selected on each occasion, wherein the bottle and the closing device are coupled to close the bottle;

c) selectively transferring the powder component C2 from the closing device 12, 32 to the bottle 11, 31;

d) mixing or dispersing the liquid component C1 with the powder component C2 inside the bottle 11, 31.

FIG. 1 shows a block diagram used to describe the sequence of operating steps of a method in accordance with the present description: each block summarizes in a synthetic manner each step of the process starting from step a) to the final step d), which ends by obtaining a liquid composition, or drink, suitable for a specific metabolic or non-metabolic disorder, according to needs.

Figures 2, 3:
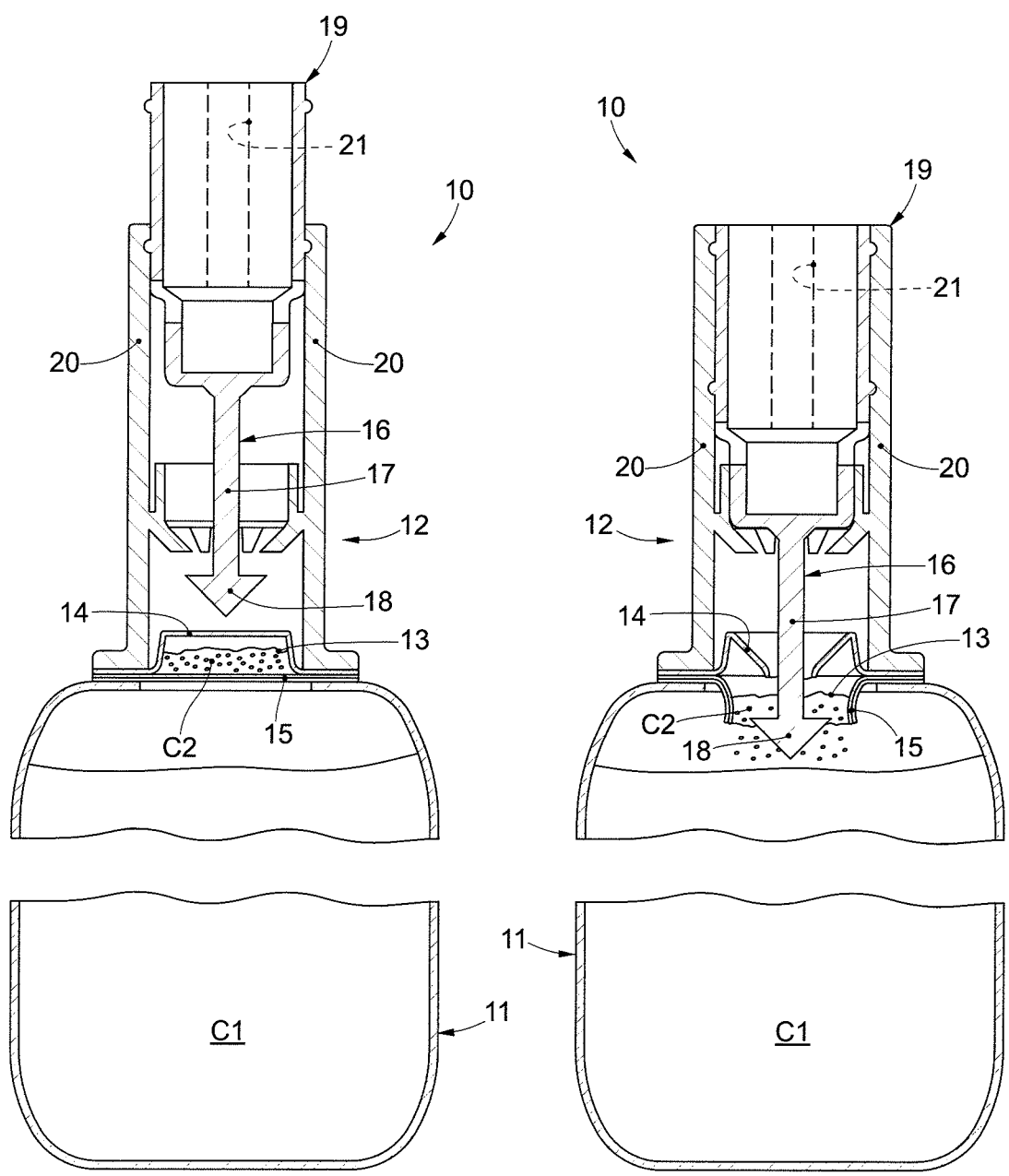
FIG. 2 is a cross section view of embodiments of a device according to the present description.
FIG. 3 is a cross section of FIG. 2.

FIG. 2 shows by way of non-restrictive example a possible embodiment of a containing device 10 comprising a bottle 11 provided with a closing device 12; the device 10 can be used to execute the method for preparing a drink in accordance with the present invention.

In accordance with step a) of the method described, the bottle 11 is filled with a liquid component C1 having a pre-determined composition irrespective of the type of metabolic or non-metabolic disorder. Preferably, in the case of a metabolic disorder for example, it is an aqueous solution comprising universally metabolized mineral salts, carbohydrates, flavors and amino acids.

According to step b) of the method described, a powder component C2 is disposed inside the closing device 12: the component C2 has a variable composition according to the specific disorder.

The closing device 12 comprises, in its bottom portion, a tank 13 suitable to keep the powder component C2 hermetically sealed, so as not to come into contact with the humidity of the air. The tank 13 has sizes such as to contain a pre-determined quantity of powder and comprises an upper layer 14 and a lower layer 15, both perforable. Preferably, the tank 13 is of the blister type with a flat surface lamina (the lower layer 15) sealed to a second lamina which forms the upper layer 14.

The closing device 12 comprises a perforation element 16, consisting of a longitudinal rod 17 and a pointed end 18: the longitudinal rod 17 connects the pointed end 18 with a control element 19 located on the upper part of the closing device 12.

The control element 19 can slide downward, inserting itself between the lateral walls 20 of the closing device 12: therefore, by manual pressure on the control element 19, a user can lower the control element 19 by moving downward the perforation element 16 as well. In this way, the pointed end 18 first impacts against the upper layer 14 and subsequently against the lower layer 15 of the blister-type tank 13, causing it to break.

The control element 19 can have different configurations, depending on the type of closing device 12 to which it is applied. In the embodiment of FIGS. 2-3, the control element 19 is provided with a cylindrical cavity 21 inside it, through which the drink can flow once it has been prepared, and then be taken by a user.

FIG. 2 shows the situation in which the tank 13 containing the powder component C2 is intact and in which the liquid component C1 is kept separate from the powder component C2: this occurs throughout the whole storage time of the two components C1 and C2, that is, until a user affected by a specific disorder presses on the control element 19 so as to lower the perforation element 16 and cause the tank 13 to break, in order to prepare the specific drink for that pathology.

FIG. 3 shows one of the possible embodiments of step c) of the method according to the present invention and provides to transfer the powder component C2 from the tank 13 into the bottle 11 to prepare the subsequent mixing step d) of the two components C1 and C2.

The control element 19 is moved downward by the manual pressure of a user, so that the perforation element 16 impacts against the upper layer 14 and the lower layer 15 of the blister-type tank 13, causing it to break. In this way, the powder component C2, no longer sealed inside the tank 13, is transferred inside the bottle 11 and comes into contact with the liquid component C1, as shown in FIG. 3.

Finally, the mixing step d) of the two components C1 and C2 follows, which can be carried out simply by shaking the device 10 manually.

Figure 4:
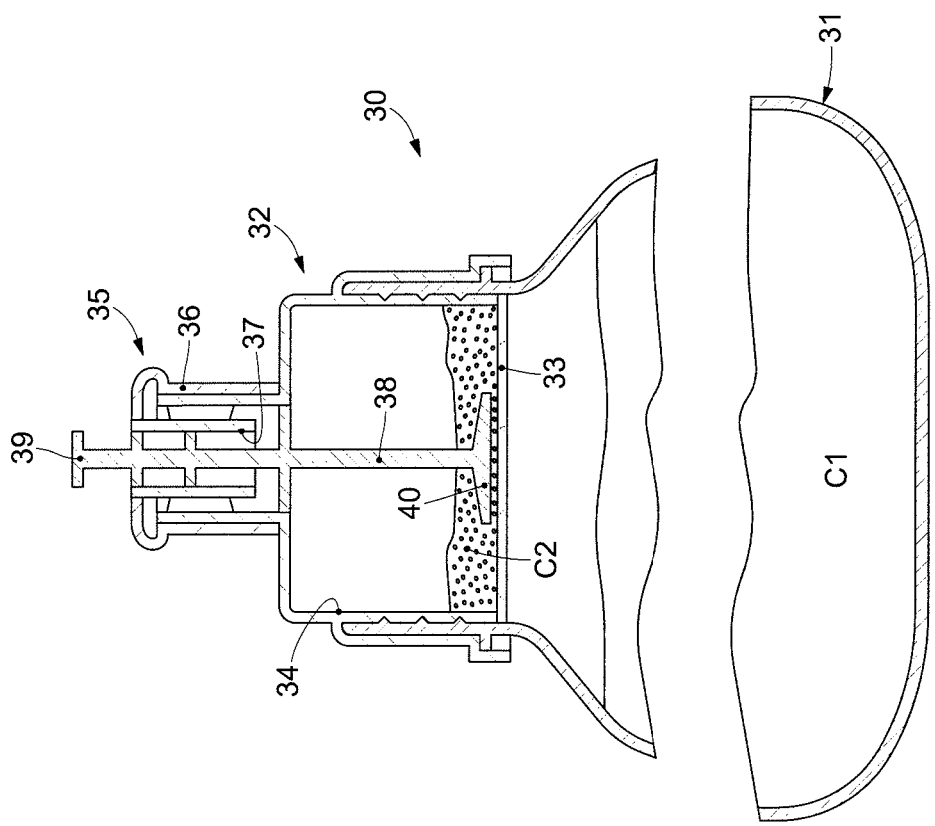
FIG. 4 is a cross section of other embodiments according to the present description.

FIG. 4 shows a second embodiment of a containing device 30 comprising a bottle 31 provided with a closing device 32, the device 30 being suitable to implement the method for preparing a drink according to the invention. As shown in this drawing, the bottle 31 and the closing device 32 are separated by a separation membrane 33, consisting for example of a polyethylene-aluminum poly-coupled film.

The bottle 31 is filled with the liquid component C1 having a pre-determined composition irrespective of the type of disorder, while a powder component C2 is introduced into the closing device 32. As we said, the component C2 has a variable composition depending on the specific metabolic or non-metabolic disorder, according to needs.

The lower part of the closing device 32 consists of a cylindrical chamber 34, inside which the powder component C2 is introduced and stored before it is mixed with the liquid component C1. The cylindrical chamber 34 is hermetically sealed, so that the humidity of the air does not come into contact with the powder component C2.

The upper part of the closing device 32 consists of a control element 35, positioned above the cylindrical chamber 34. The control element 35 comprises the following components: an annular covering cap 36, a tubular chamber 37 and a mobile thruster 38.

The mobile thruster 38 is disposed along the central axis of the control element 34 and is able to slide vertically along the internal walls of the tubular chamber 37. It can move downward following a manual pressure exerted on the button 39 positioned at the upper end of the mobile thruster 38.

A thrust member 40 is disposed at the lower end of the thruster 38, so that the downward pressure of the button 39 causes a pressure of the thrust element 40 against the separation membrane 33.

FIG. 4 shows the situation in which the liquid component C1 is kept separate from the powder component C2: this occurs throughout the whole storage time of the two components C1 and C2, that is, until a user presses the button 39 to lower the thruster 38 and cause the separation membrane 33 to break.

Figure 5:
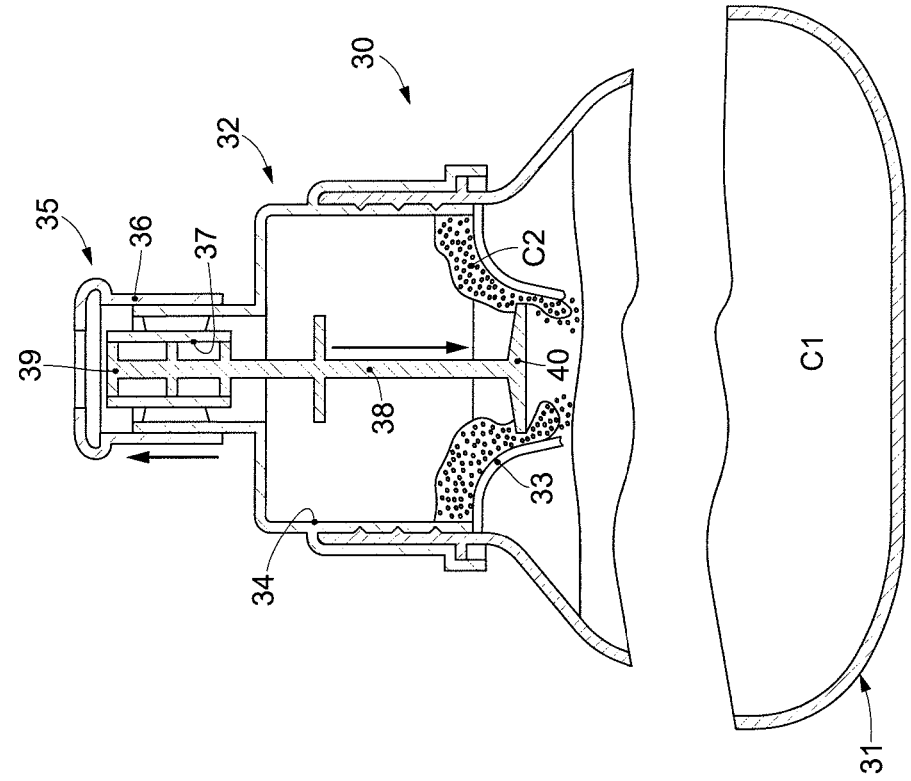
FIG. 5 is a cross section of FIG. 4.

FIG. 5 shows how the powder component C2 is transferred inside the bottle 31 (step c) of the method claimed). The control element 35 is moved downward by the manual pressure of a user, so that the thruster 38 impacts against the separation membrane 33, causing it to break. In this way, the powder component C2 is transferred inside the bottle 11 and comes into contact with the liquid component C1. The mixing step of the two components C1 and C2 can be achieved simply by shaking the device 30 manually.

Once the two components have been mixed, the upward movement of the covering cap 36 in the direction indicated by the arrow (FIG. 5) allows to open passage channels inside the closing device 32: the prepared drink can flow through these passage channels, and then be taken by a user without removing the closing device 32.

The transfer means to carry out step c) of the method, described above in relation to FIGS. 2-5, are only examples of implementation, and not restrictive of the possible transfer means that can be used in the method for preparing a drink according to the invention. There are other transfer means which can be used, for example, the device to release a powdered substance into a container as described in patent EP-A-1.976.768 and the closing device for a container as described in WO-A-2012/035417. These devices, provided with a bottle and corresponding closing device, are equally effective to transfer the powder component C2 into the bottle, as provided by step c) of the method claimed.

As we said, in some embodiments, the liquid component C1 is a pre-determined aqueous solution irrespective of the type of metabolic disorder. For example, it includes mineral salts, carbohydrates and universally metabolizable amino acids. In some embodiments, particularly usable in the case of metabolic disorders, the powder component C2 includes vitamins and a specific mixture of amino acids with the exclusion of the specific amino acid responsible for the metabolic disorder.

Hereafter, we will describe embodiments of suitable compositions of the powder component C2 based on the specific metabolic disorder from which the patient suffers.

Therefore, according to a first variant embodiment of the device 10 and method for the preparation of a liquid composition or drink described here, if the metabolic disorder is phenylketonuria, the powder component C2 comprises the following mixture of amino acids: isoleucine, leucine, methionine, threonine, tyrosine and valine, and does not include phenylalanine.

According to a second variant embodiment of the device 10 and method described here, if the metabolic disorder is tyrosinemia, the powder component C2 comprises the following mixture of amino acids: isoleucine, leucine, methionine, threonine and valine, and does not include tyrosine.

According to a third variant embodiment of the device 10 and method described here, if the metabolic disorder is homocystinuria, the powder component C2 comprises the following mixture of amino acids: isoleucine, leucine, threonine, tyrosine, valine and phenylalanine, and does not include methionine.

According to a fourth variant embodiment of the device 10 and method described here, if the metabolic disorder is maple syrup urine disease, the powder component C2 comprises the following mixture of amino acids: methionine, threonine, tyrosine and phenylalanine, and does not include leucine, isoleucine, and valine.

According to a fifth variant embodiment of the device 10 and of the method described here, if the metabolic disorder is methylmalonic acidemia or propionic acidemia, the powder component C2 comprises the following mixture of amino acids: leucine, tyrosine and phenylalanine, and does not include isoleucine, valine, methionine and threonine.

According to a sixth variant embodiment of the device 10 and method described here, if the metabolic disorder is isovaleric acidemia, the powder component C2 comprises the following mixture of amino acids: isoleucine, methionine, threonine, tyrosine, valine and phenylalanine, and does not include leucine.

Another embodiment concerns a device, a kit and a method for diversifying the liquid compositions, or drinks, suitable for a specific metabolic disorder (for example homocystinuria), based on the aromatic substances added. In fact, starting from the premise that it is possible to diversify the composition of the powder component C2 while keeping the composition of the liquid component C1 unchanged, for each disorder it is possible to introduce in step b) a powder component C2 containing a specific flavoring substance, keeping the other components unaltered.

This would lead to the production of a series of liquid compositions, or drinks, suitable to be taken by a person affected by a specific metabolic disorder, but diversified with respect to their taste, which depends on the aromatic substance inserted into the powder component. This series of liquid compositions or drinks can be obtained by means of a kit of devices 10, 30 in series, in which each closing device 12, 32 contains a powder component C2 whose composition differs only in the flavoring substances.

Another aspect of the present invention therefore concerns a kit of devices 10, 30 for the preparation and oral administration of a series of liquid compositions for the treatment of persons affected by metabolic or non-metabolic disorders, each device 10, 30 comprising:

- a bottle 11, 31 containing a liquid component C1 having a pre-determined and non-variable composition, irrespective of the type of disorder; for example, the liquid component C1, in the case of metabolic disorders, includes mineral salts, carbohydrates and a mixture of amino acids without the specific amino acid responsible for the specific metabolic disorder;
- a closing device 12, 32 configured to close the bottle 11, 31 and inside which there is a powder component C2 having a variable composition according to the disorder and functional for the treatment of the specific disorder selected on each occasion and also comprising one or more flavoring substances; for example, the powder component C2 includes vitamins, one or more flavoring substances, and possibly proteins and carbohydrates;
- transfer means associated with the closing device 12, 32 and configured to transfer the powder component C2 from the closing device 12, 32 to the bottle 11, 31, for the purpose of mixing or dispersing the liquid component C1 with the powder component C2 inside the bottle 11, 31 to obtain the liquid composition;

wherein the powder component C2 differs between the closing devices 12, 32 of the devices 10, 30 only in at least one flavoring substance, while the other ingredients of its composition remain unaltered.

Consequently, diversified flavoring substances are added to each containing device 10, 30 of the kit described above, so as to be able to diversify the taste of the drinks prepared for a person affected by a specific metabolic or non-metabolic disorder, according to the case.

In possible implementations, the flavoring substances can be chosen from natural flavors, identical natural flavors, or dry extracts of fruit in powder form (for example citrus fruit, peach, cherry, strawberry, red fruits such as blueberries or currants), plants, vegetables, officinal plants (for example chamomile, fennel, vanilla, nettle, mint).

It is clear that modifications and/or additions of parts can be made to the device 10, method and kit for the preparation and oral administration of a composition, for the treatment of persons affected by metabolic or non-metabolic disorders as described heretofore, without departing from the field and scope of the present invention.

In particular, the device, the method and the kit according to the embodiments described here can be used, suitably selecting the powder component present in the closing device and the liquid component present in the bottle, also for the preparation and oral administration of liquid compositions suitable for the treatment of people or individuals affected by non-metabolic disorders, in particular: kidney diseases and pathologies such as drug-resistant epilepsy. The Applicant has hypothesized that in the future also pathologies such as some gastrointestinal disorders, or some types of cancer, as well as Alzheimer's disease could be treated with this device.

It is also clear that, although the device, method and kit according to the present invention has been described with reference to the attached drawings, a person of skill in the art shall certainly be able to achieve many other equivalent forms of device and method, having the characteristics as set forth in the claims and hence all coming within the field of protection defined thereby.

In the following claims, the sole purpose of the references in brackets is to facilitate reading: they must not be considered as restrictive factors with regard to the field of protection claimed in the specific claims.

The invention claimed is:

1. A Device for the preparation and oral administration of a liquid composition formed by a liquid component (C1) and a component in powder form (C2), for the treatment of persons affected by metabolic disorders, characterized in that said metabolic disorders are chosen from a group consisting of: phenylketonuria, tyrosinemia, homocystinuria, maple syrup urine disease, methylmalonic acidemia, propionic acidemia and isovaleric acidemia and in that said device comprises:
    a) a bottle (11, 31) inside which there is a liquid component (C1) with a pre-established and non-variable composition, irrespective of the type of metabolic disorder to be treated, wherein said liquid component (C1) is an aqueous solution comprising mineral salts, carbohydrates, aromas and universally metabolizable amino acids;
    b) a closing device (12, 32) configured to close said bottle (11, 31) and inside which there is a component in powder form (C2) with a variable composition according to the metabolic disorder and functional for the treatment of the specific metabolic disorder selected on each occasion, wherein said component in powder form (C2) comprises vitamins and a mix of amino acids without the specific amino acid responsible for said metabolic disorder to be treated chosen from said metabolic disorders, said component in powder form (C2) is hermetically sealed in a tank (13) or cylindrical chamber (34) inside said closing device (12, 32);
    c) transfer means associated with said closing device (12, 32) and configured to selectively transfer said component in powder form (C2) from said closing device (12, 32) to said bottle (11, 31) so as to mix or disperse said liquid component (C1) with said component in powder form (C2) inside said bottle (11, 31) in order to obtain said liquid composition.

2. The device as in claim 1, wherein said metabolic disorder is phenylketonuria and said component in powder form (C2) comprises the following mix of amino acids: isoleucine, leucine, methionine, threonine, tyrosine and valine, and has no phenylalanine.

3. The device as in claim 1, wherein said metabolic disorder is tyrosinemia and said component in powder form (C2) comprises the following mix of amino acids: isoleucine, leucine, methionine, threonine and valine, and has no tyrosine.

4. The device as in claim 1, wherein said metabolic disorder is homocystinuria and said component in powder form (C2) comprises the following mix of amino acids: isoleucine, leucine, threonine, tyrosine, valine and phenylalanine, and has no methionine.

5. The device as in claim 1, wherein said metabolic disorder is maple syrup urine disease and said component in powder form (C2) comprises the following mix of amino acids: methionine, threonine, tyrosine and phenylalanine, and has no leucine, isoleucine or valine.

6. The device as in claim 1, wherein said metabolic disorder is methylmalonic acidemia or propionic acidemia and in that said component in powder form (C2) comprises the following mix of amino acids: leucine, tyrosine and phenylalanine, and has no isoleucine, valine, methionine and threonine.

7. The device as in claim 1, wherein said metabolic disorder is isovaleric acidemia and in that said component in powder form (C2) comprises the following mix of amino acids: isoleucine, methionine, threonine, tyrosine, valine and phenylalanine and has no leucine.

8. A method for the preparation of a liquid composition formed by a liquid component (C1) and a component in powder form (C2), for oral administration for the treatment of persons affected by metabolic disorders, characterized in that said metabolic disorders are comprised in a group consisting of: phenylketonuria, tyrosinemia, homocystinuria, maple syrup urine disease, methylmalonic acidemia, propionic acidemia and isovaleric acidemia and in that said method comprises the following steps:
   a) filling a bottle (11, 31) with a liquid component (C1) with a pre-established and non-variable composition irrespective of the type of disorder to be treated, wherein said liquid component (C1) is an aqueous solution comprising mineral salts, carbohydrates, aromas and universally metabolizable amino acids;
   b) making available a closing device (12, 32) of said bottle (11, 31), there being present inside said closing device (12, 32) a component in powder form (C2) with a variable composition according to the metabolic disorder to be treated and functional for the treatment of the specific disorder selected on each occasion, wherein said bottle (11, 31) and said closing device (12, 32) are coupled to close said bottle (11, 31), wherein said component in powder form (C2) comprises vitamins and a mix of amino acids responsible for the specific metabolic disorder to be treated comprised in said metabolic disorders, said component in powder form (C2) is hermetically sealed in a tank (13) or cylindrical chamber (34) inside said closing device (12, 32);
   c) selectively transferring said component in powder form (C2) from said closing device (12, 32) to said bottle (11, 31);
   d) mixing or dispersing said liquid component (C1) with said component in powder form (C2) inside said bottle (11, 31).

9. The method of claim 8, wherein said metabolic disorder is phenylketonuria and said component in powder form (C2) comprises the following mix of amino acids: isoleucine, leucine, methionine, threonine, tyrosine and valine and has no phenylalanine.

10. The method of claim 8, wherein said metabolic disorder is tyrosinemia and said component in powder form (C2) comprises the following mix of amino acids: isoleucine, leucine, methionine, threonine and valine and has no tyrosine.

11. The method of claim 8, wherein said metabolic disorder is homocystinuria and said component in powder form (C2) comprises the following mix of amino acids: isoleucine, leucine, threonine, tyrosine, valine and phenylalanine and has no methionine.

12. The method of claim 8, wherein said metabolic disorder is maple syrup urine disease and said component in powder form (C2) comprises the following mix of amino acids: methionine, threonine, tyrosine and phenylalanine and has no leucine, isoleucine or valine.

13. The method of claim 8, wherein said metabolic disorder is methylmalonic acidemia or propionic acidemia and in that said component in powder form (C2) comprises the following mix of amino acids: leucine, tyrosine and phenylalanine, and has no isoleucine, valine, methionine or threonine.

14. The method of claim 8, wherein said metabolic disorder is isovaleric acidemia and in that said component in powder form (C2) comprises the following mix of amino acids: isoleucine, methionine, threonine, tyrosine, valine and phenylalanine and has no leucine.

15. A kit of containing devices (10, 30) for the preparation of a series of liquid compositions formed by a liquid component (C1) and a component in powder form (C2), for the treatment of persons affected by metabolic disorders comprised in a group consisting of: phenylketonuria, tyrosinemia, homocystinuria, maple syrup urine disease, methylmalonic acidemia, propionic acidemia and isovaleric acidemia, each containing device (10, 30) comprising:
   a bottle (11, 31) inside which there is a liquid component (C1) with a pre-established and non-variable composition, irrespective of the type of metabolic disorder to be treated, wherein said liquid component (C1) is an aqueous solution comprising mineral salts, carbohydrates, aromas and universally metabolizable amino acids;
   a closing device (12, 32) configured to close said bottle (11, 31) and inside which there is a component in powder form (C2) with a variable composition according to the metabolic disorder and functional for the treatment of the specific metabolic disorder selected on each occasion and also comprising one or more aromatizing substances, wherein said component in powder form (C2) comprises vitamins and a mix of amino acids without the specific amino acid responsible for the metabolic disorder to be treated chosen from said metabolic disorders, said component in powder form (C2) is hermetically sealed in a tank (13) or cylindrical chamber (34) inside said closing device (12, 32);
   transfer means associated with said closing device (12, 32) and configured to transfer said component in powder form (C2) from said closing device (12, 32) to said bottle (11, 31) so as to mix or disperse said liquid component (C1) with said component in powder form (C2) inside said bottle (11, 31) in order to obtain said liquid composition;
   wherein the component in powder form (C2) differs, between said closing devices (12, 32), only in at least one aromatizing substance, the other ingredients of the composition remaining unaltered.

16. The kit of containing devices (10, 30) of claim 15, wherein said aromatizing substances are chosen from natural aromas, identical natural aromas, powdered dry extracts of fruit, powdered dry extracts of vegetables or plants.

* * * * *